(12) United States Patent
Hu

(10) Patent No.: US 9,108,907 B1
(45) Date of Patent: Aug. 18, 2015

(54) PROCESS FOR THE PRODUCTION OF TAURINE FROM ETHANOL

(71) Applicant: Songzhou Hu, Princeton, NJ (US)

(72) Inventor: Songzhou Hu, Princeton, NJ (US)

(*) Notice: Subject to any disclaimer, the term of this patent is extended or adjusted under 35 U.S.C. 154(b) by 0 days.

(21) Appl. No.: 13/999,203

(22) Filed: Jan. 29, 2014

(51) Int. Cl.
  *C07C 303/22* (2006.01)

(52) U.S. Cl.
  CPC .................................. *C07C 303/22* (2013.01)

(58) Field of Classification Search
  None
  See application file for complete search history.

(56) References Cited

U.S. PATENT DOCUMENTS 3,637,793 A * 1/1972 Lamberti ....................... 562/101
4,435,328 A * 3/1984 Lamberti et al. ................ 554/92

OTHER PUBLICATIONS

Manual of Patent Examining Procedure (MPEP) Ninth Edition, Mar. 2014 section 714 "Amendments to the Claims".*
Machine Translation of CN10148669 taken from espacnet.com.*
Breslow et al, Synthesis of Sodium Ethylenesulfonate from Ethanol J. Am.Chem.Soc., 1954, vol. 76, pp. 5361-5363.

* cited by examiner

*Primary Examiner* — Karl J Puttlitz

(57) ABSTRACT

The present invention discloses a process for the preparation of taurine from ethionic acid and ethanol by way of ethanol-derived ethionic acid by the ammonolysis of ethionic acid and by the ammonolysis of sodium isethionate and sodium vinyl sulfonate, key intermediates prepared from ethionic acid.

2 Claims, 3 Drawing Sheets

Production of Taurine via Ethionic Acid

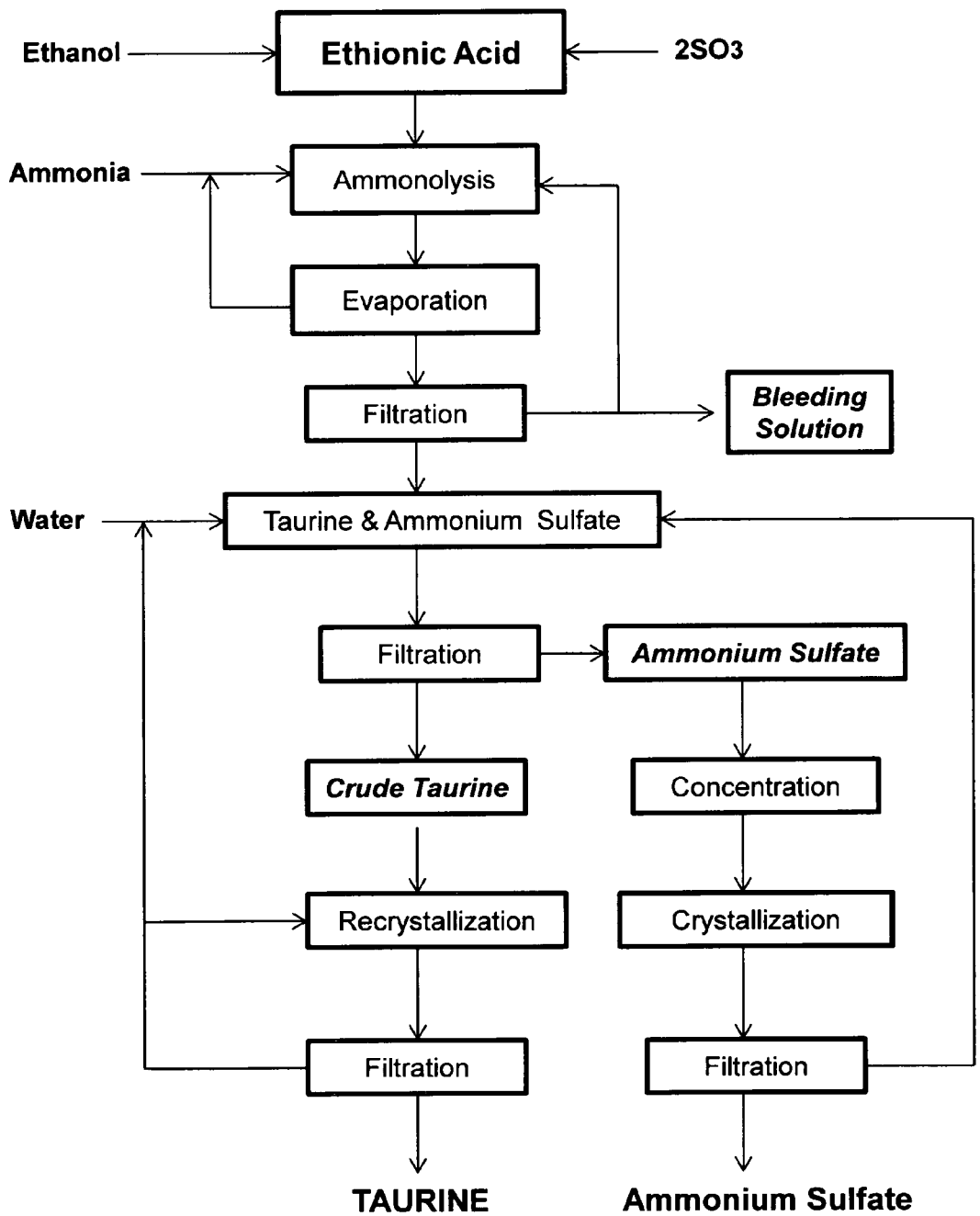
Fig. 1. Production of Taurine via Ethionic Acid

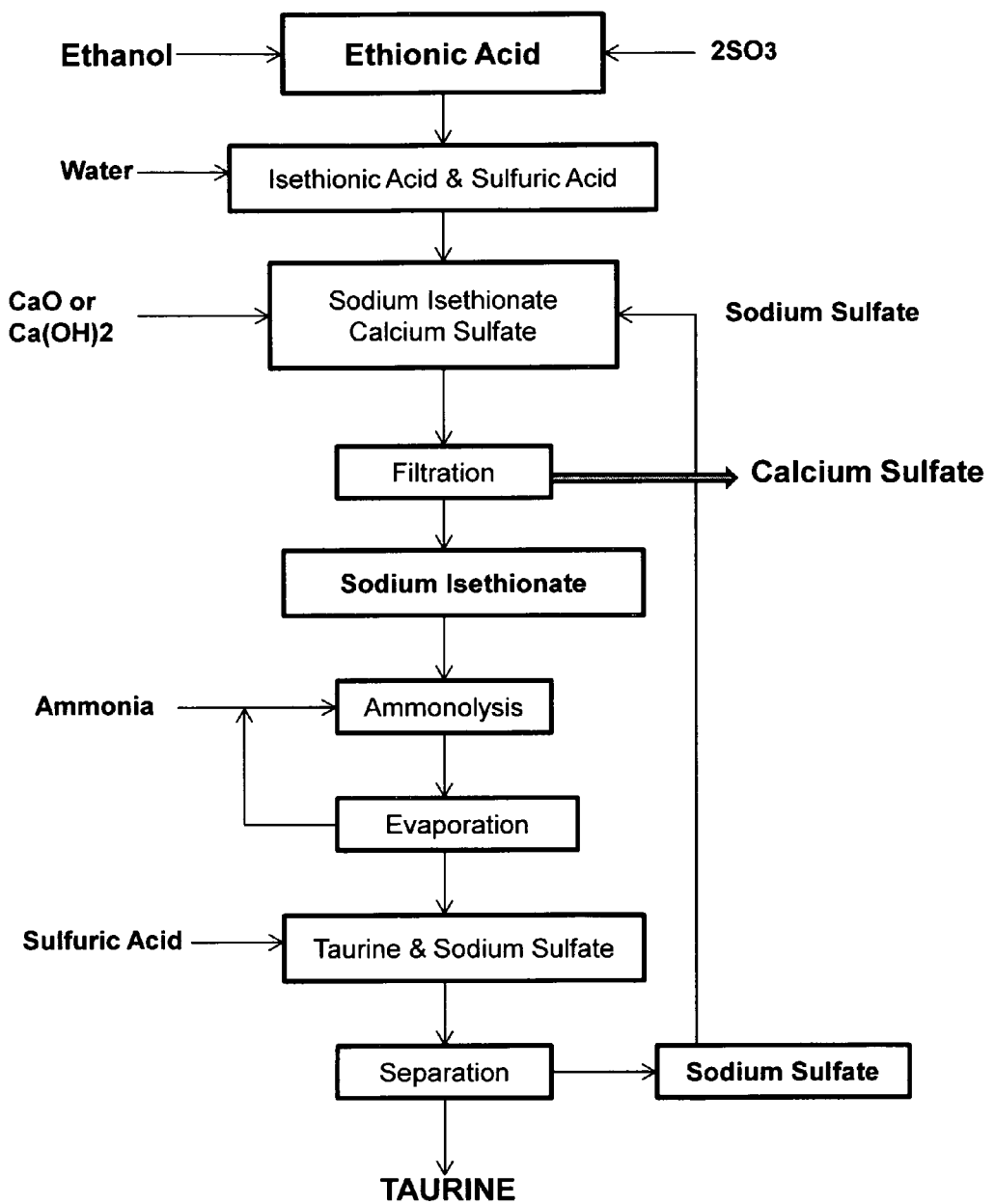
Fig. 2. Production of Taurine via Sodium Isethionate

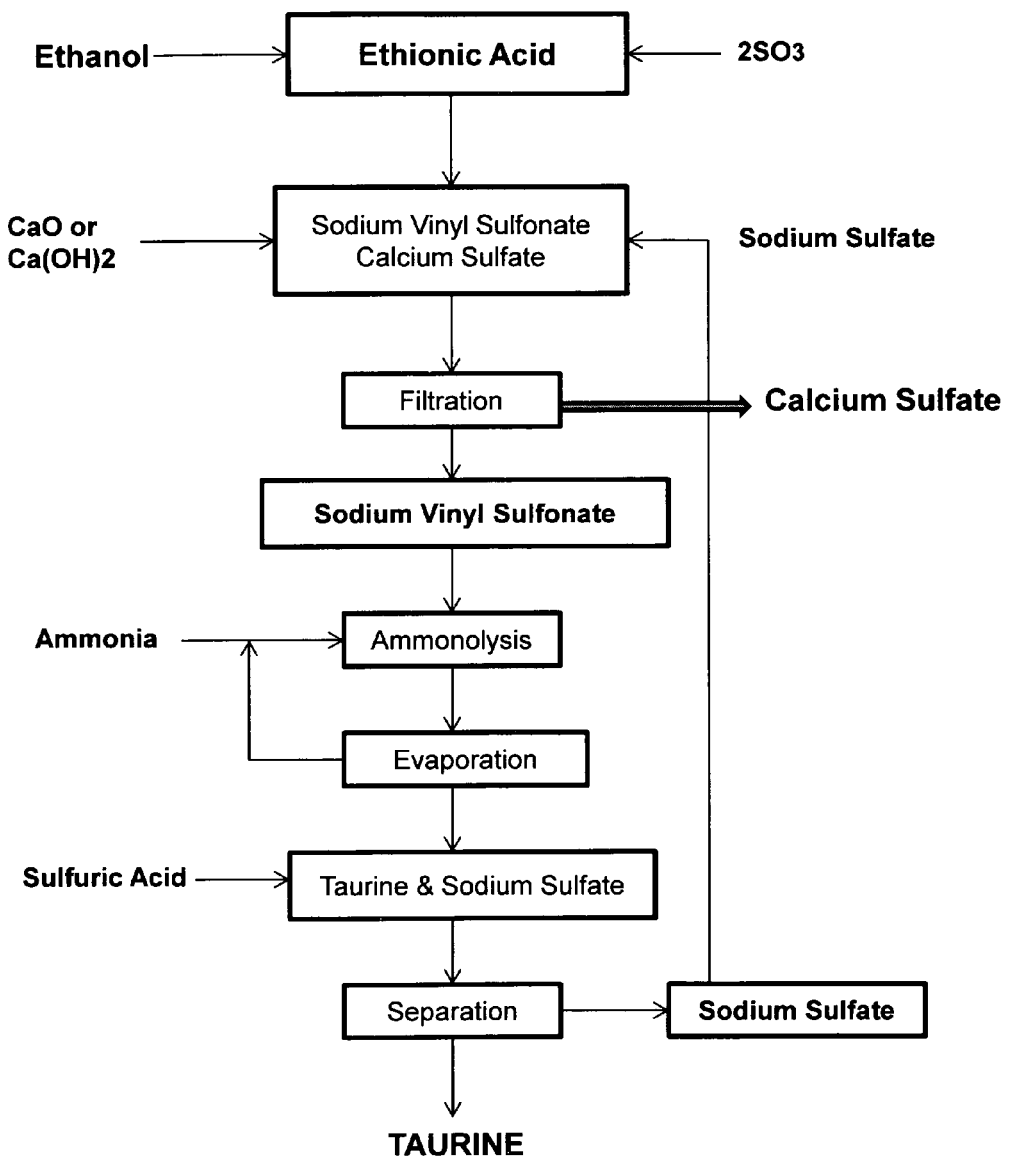
Fig. 3. Production of Taurine via Sodium Vinyl Sulfonate

PROCESS FOR THE PRODUCTION OF TAURINE FROM ETHANOL

TECHNICAL FIELD

This invention relates generally to taurine and more particularly to a process for the production of taurine from ethionic acid and ethanol by way of ethanol-derived ethionic acid.

BACKGROUND OF THE INVENTION

Taurine can be referred to as 2-aminoethanesulfonic acid and is one of the amino sulfonic acids found in the tissues of many animals. Taurine is an extremely useful compound because it has such pharmacological effects as detoxification effect, fatigue-relieving effect and nourishing and tonifying effect. As a result, taurine finds wide applications as an essential ingredient for human and animal nutrition.

Taurine is currently produced in an amount of over 50,000 tons per year from ethylene oxide and monoethanolamine, both of which are petroleum derived chemicals. In addition to their ever increasing cost, these two starting materials are toxic and for ethylene oxide difficult to handle. An alternate process for producing taurine from non-petroleum chemical is, therefore, desirable. Such a process would be even more valuable if taurine could be produced at a lower and more stable cost.

Ethanol is easily available at reasonable cost from natural sources by fermentation as it is produced in large quantity as a fuel additive and as an industrially important chemical. Furthermore, an industrially applicable process for the conversion of ethanol into ethionic acid is already known (U.S. Pat. No. 3,637,793, incorporated herein, by reference). This invention discloses novel methods for the conversion of ethanol-derived ethionic acid into taurine.

The disclosed process can also be applied to the production of taurine from ethionic acid prepared from other materials such as ethylene and carbyl sulfate.

It is, therefore, an object of this invention to provide a process for producing taurine from ethanol via ethanol-derived ethionic acid, which is economical and more competitive than current industrial processes using ethylene oxide and monoethanolamine as starting materials.

It is another object of the present invention to disclose a process for the conversion of ethionic acid into sodium isethionate and sodium vinyl sulfonate, key intermediates for producing taurine from ethionic acid by a combined use of calcium oxide/calcium hydroxide and sodium sulfate as alkaline media.

It is a further object of the present invention to disclose a process for the cyclic use of alkali metal ions, more specifically, sodium ion in the form of sodium sulfate, sodium isethionate, and sodium ethionate, in the production of taurine from ethionic acid via key intermediates of sodium isethionate and sodium vinyl sulfonate.

DESCRIPTION OF THE DRAWINGS

FIG. 1 is a flow chart showing the first embodiment of the present invention as a block diagram wherein taurine is produced by direct ammonolysis of ethanol-derived ethionic acid.

FIG. 2 is a flow chart showing the second embodiment of the present invention as a block diagram wherein taurine is produced by ammonolyis of sodium isethionate intermediate prepared from ethanol-derived ethionic acid.

FIG. 3 is a flow chart showing the third embodiment of the present invention as a block diagram wherein taurine is produced by ammonolyis of sodium vinylsulfate intermediate prepared from ethanol-derived ethionic acid.

DESCRIPTION OF THE INVENTION

In accordance with the present invention, there are disclosed three preferred embodiments for producing taurine from ethionic acid and more specifically from ethanol by way of ethanol-derived ethionic acid. These three embodiments are schematically illustrated in FIGS. 1 to 3 as a block diagram.

In the first preferred embodiment of the present invention, ethionic acid is reacted with an aqueous solution of excess ammonia to afford ammonium ethionate. The molar ratio of ammonia to ethionic acid can be in the range of 5 to 15, more preferably in the range of 8 to 10. Too little ammonia increases the formation of ditaurine, a byproduct, while more ammonia is desirable for the reaction, too much ammonia increases the process cost in the recovery of excess ammonia. The reactions are described as follows:

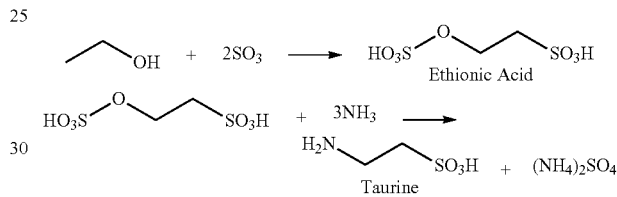

When the aqueous ammonia solution of ammonium ethionate is subjected to the ammonolysis reaction at a temperature of 100 to 250° C., preferably from 130 to 220° C., at a pressure from the autogenous to 250 bar, preferably from 100 to 150 bar, ammonium ethionate is converted to taurine and ammonium sulfate, along with the formation of some ammonium isethionate. The ammonolysis can also be carried out in the presence of catalyst such as the alkaline salts of sodium, potassium and lithium. Such salts are sodium hydroxide, potassium hydroxide, lithium hydroxide, sodium carbonate, potassium carbonate, lithium carbonate, sodium sulfate, sodium sulfite, potassium sulfate, potassium sulfite. Any one or a combination of two or more these salts can be used as catalyst to influence the reaction.

It is surprising to disclose in the present invention that no acid neutralization of the aqueous solution is needed when excess ammonia is removed first by flash distillation, then by evaporation under vacuum. The concentrated solution shows a pH of 5-6, and upon cooling, taurine is crystallized and can be separated by filtration. Further concentration of the mother liquor results in the crystallization of a mixture of taurine and ammonium sulfate. The separation of taurine and ammonium sulfate can be accomplished according to a process disclosed in the Co-pending application, titled Cyclic Process for the Production of Taurine from Monoethanolamine, incorporated herein in FIG. 1. Crude taurine is upgraded to a product of pharmaceutical grade after one or more recrystallization in deionized water.

In the second preferred embodiment, ethionic acid, more specifically, ethanol-derived ethionic acid, is first converted to sodium isethionate, which is then subjected to the ammonolysis reaction to yield sodium taurinate. The process is schematically illustrated in FIG. 2 and the reaction schemes are as follows:

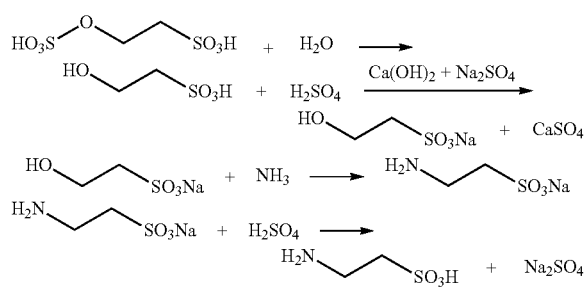

Production of alkali isethionate from ethionic acid is already known (U.S. Pat. No. 4,435,328, incorporated herein, by reference). According to U.S. Pat. No. 4,435,328, ethionic acid is first diluted with water, then heated to complete the hydrolysis to obtain an aqueous solution of isethionic acid and sulfuric acid, which can be then neutralized with a mixture of calcium hydroxide and alkali metal hydroxide. The preferred method is the combined use of calculated amount of calcium hydroxide and sodium hydroxide. Using this process, sulfuric acid is converted into calcium sulfate and subsequently removed by filtration form the aqueous solution of sodium isethionate.

The present invention discloses a much more preferred process for preparing alkali metal isethionate by a combined use of calcium hydroxide/calcium oxide/calcium carbonate and alkali metal sulfate. Alkali metal sulfate can be lithium sulfate, sodium sulfate, and potassium sulfate.

Ethionic acid is first diluted with water and then hydrolyzed by heating to obtain an aqueous solution containing isethionic acid and sulfuric acid, to which alkali metal sulfate is added. The amount of alkali metal sulfate can be calculated on the basis of substantially complete hydrolysis of ethionic acid into an equimolar mixture of isethionic acid and sulfuric acid. After the addition of alkali metal sulfate, sufficient calcium oxide or calcium hydroxide is introduced into the aqueous solution so that the pH of the mixture is brought within the range of about 8.0 to 9.0. An excess amount of alkali metal sulfate can be beneficially added into the solution as it does not interfere with the subsequent reaction of sulfuric acid with calcium hydroxide and as long as it does not affect the quality of the obtained alkali metal isethionate for commercial purpose. The resulted precipitate of calcium sulfate is easily separated from the aqueous solution of alkali metal isethionate by filtration of the slurry and washing of the wet filtration cake. The thus obtained aqueous solution of alkali metal isethionate can be concentrated to a desired concentration or used as such in the subsequent step of ammonolysis.

If calcium carbonate is used as a source of calcium, the sequence of addition needs to be altered. After ethionic acid is diluted with water and hydrolyzed into isethionic acid and sulfuric acid, calcium carbonate is carefully added the aqueous solution to form a slurry of calcium sulfate and calcium isethionate. Then calculated or excess amount of alkali metal sulfate is introduced into the reaction system to replace calcium in calcium isethionate with alkali metal in alkali metal sulfate.

For the production of taurine, sodium sulfate is preferably used, but other alkali metal sulfates are equally suitable. In the drawings and following description, only sodium and sodium sulfate are used in replace of alkali metal and alkali metal sulfate to describe the process.

In comparison with U.S. Pat. No. 4,435,328, the process for preparing sodium isethionate disclosed in the present invention is operationally simpler, and more economical. The process requires only the monitoring of the pH in the reaction system. Moreover, the costly base of sodium hydroxide is replaced with the inexpensive calcium oxide or calcium hydroxide, and sodium is introduced into the product in the form of sodium sulfate, which by itself is a byproduct in the production of taurine.

It is apparent from FIG. 2 that sodium sulfate is recycled continuously in the production of taurine from ethionic acid by way of intermediate sodium isethionate, thus eliminating an otherwise waste discharge. An added advantage is the increased recovery yield of taurine, since sodium sulfate separated from its mixture with taurine invariably contains a small amount of taurine. This cyclic use of sodium sulfate in the production process ensures that no trace of taurine produced is discharged in the waste stream.

For the production of taurine, the use of excess amount of sodium sulfate in the preparation of sodium isethionate is preferable, as the excess of sulfate drastically reduce the residual amount of calcium in the aqueous solution of sodium isethionate. Moreover, sodium sulfate also functions as a catalyst for the ammonolysis of sodium isethionate and increases the yield of taurine.

To produce taurine, sodium isethionate is subjected to the ammonolysis reaction in the presence of excess amount of ammonia, the molar ratio of ammonia to isethionate being in the range of 5 to 15, and more preferably 6-8. The ammonolysis reaction is carried out at a temperature of 160 to 250° C., more preferably 220-250° C. The pressure can be from the autogenous to 250 bar, preferably from 160 to 200 bar. The reaction can be carried out discontinuously, semicontinuously, or continuously.

It has been found in the present invention that the reaction time of ammonolysis of sodium isethionate can be drastically shortened and the yield of taurine increased by the use of catalyst, which can be any one or a combination of two or more of the alkaline salts, such as sodium hydroxide, potassium hydroxide, sodium carbonate, potassium carbonate, sodium sulfate, and potassium sulfate, sodium sulfite, and sodium sulfite. Among these salts, sodium hydroxide and its combination with sodium sulfate are found to be most effective.

After excess ammonia is removed and recovered for further use, an aqueous solution of sodium taurinate is obtained. Neutralization with sulfuric acid results in the formation of a mixture of taurine and sodium sulfate, which can be separated by any methods known in prior arts. Crude taurine can be purified by one or more recrystallization in deionized water to afford a final product of pharmaceutical grade, while sodium sulfate is recycled back to the production of sodium isethionate.

Neutralization of sodium taurinate can also be achieved by using dilute ethionic acid or its hydrolyzed mixture of isethionic acid and sulfuric acid. When these acids are used, their sodium salts are recycled to prepare sodium isethionate after separation of taurine. This novel way of neutralization eliminates the use of sulfuric acid and thus further reduces production cost.

In the third preferred embodiment, schematically illustrated in FIG. 3, ethionic acid, more particularly ethanol-derived ethionic acid, is first transformed into sodium vinyl sulfonate, which is then subjected to ammonolysis to yield sodium taurinate. Neutralization with sulfuric acid and separation complete the production cycle to yield taurine and sodium sulfate. The reactions are depicted as follows:

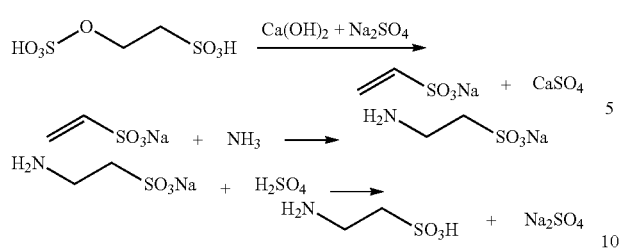

Preparation of sodium vinyl sulfonate from ethionic acid is already known (Breslow et al, J. Am. Chem. Soc., 1954, vol. 76, pp 5361-3). According to Breslow, ethionic acid, obtained from ethanol and two moles of sulfur trioxide, is added dropwise to a solution of 3.2 moles of sodium hydroxide at a temperature of 65-70° C., followed by neutralization with sulfuric acid. After cooling to crystallize sodium sulfate, a solution of sodium vinyl sulfate is obtained after filtration. The process according to this method is expensive, since so much costly sodium hydroxide is used. The product obtained by this method is of questionable quality to warrant the practice of an industrially feasible process.

The present invention provides a method of producing sodium vinyl sulfonate in which sodium vinyl sulfonate is obtained in a substantially pure form without the formation of by-products. This object is achieved by using a combination of calcium oxide/calcium hydroxide/calcium carbonate and sodium hydroxide, and more preferably by using a combination of calcium oxide/calcium hydroxide and sodium sulfate.

Sodium vinyl sulfonate is in general prepared in two stages. In the first stage, ethionic acid is carefully neutralized by calcium oxide, calcium hydroxide, or calcium carbonate to pH 7-8 while the temperature is maintained at 35-50° C. The amount of calcium oxide, calcium hydroxide, or calcium carbonate, is calculated on the molar basis of ethionic acid. The molar ratio can be in the range of 1.0 to 1.5, but preferably 1.05-1.15, since excess calcium ion will require additional sulfuric acid for its removal. In the second stage, sodium hydroxide is added to maintain a pH of 9 to 12, preferably 9-11 to complete the conversion to sodium vinyl sulfonate. The amount of sodium hydroxide required is about equimolar of ethionic acid. After the addition of sodium hydroxide, the temperature is subsequently raised to 70-150° C., more preferably 70-90° C. After cooling, the alkaline pH is adjusted to 7-8 by adding dilute sulfuric acid. The slurry is filtered to remove calcium sulfate and a solution of sodium vinyl sulfate is obtained in nearly pure form.

For the more preferable method to prepare sodium vinyl sulfonate, a combination of calcium oxide/calcium hydroxide and sodium sulfate is employed to provide the alkaline media to convert ethionic acid. In this novel process, ethionic acid and molar equivalent or more sodium sulfate are introduced into the reaction system, then calcium hydroxide is introduced to raise the pH to a range of 9-12, preferably 9-11, while maintaining the temperature at 35-50° C. in the first stage by external cooling, then to 70-150° C., more preferably 70-90° C. in the second stage. After cooling and adjusting pH with sulfuric acid, an aqueous solution of sodium vinyl sulfate is obtained after filtering off calcium sulfate.

It is apparent from FIG. 3 that cyclic use of sodium sulfate in the production of sodium vinyl sulfate and taurine affords the same advantage as those described in the process of taurine production via sodium isethionate intermediate.

It has been found that ethionic acid can also be used to neutralize the sodium taurinate to yield taurine and sodium ethionate. After the separation of taurine, sodium ethionate is combined with equimolar ethionic acid and then treated with calcium oxide/calcium hydroxide to obtain sodium vinyl sulfate. In this variation of the cyclic process, sulfuric acid is eliminated from the process and production cost is further reduced.

The present invention is more particularly described in the following examples, which are intended as illustrative only.

Example 1

Ethionic acid, 206 g, prepared according to the method of U.S. Pat. No. 3,637,793, is dropwise added to a cooled solution of 1,000 mL aqueous ammonia (25%). The solution is then placed in a 2 L autoclave and heated to 180° C. for two hours. HPLC analysis indicates there are 87.5 g of taurine formed in the solution. After excess ammonia is removed by boiling and the solution concentrated to about 500 mL under vacuum distillation. After cooling to room temperature to yield a crystalline suspension, in which the pH is 5.6. After filtration, crude taurine is obtained in an amount of 68.4 g. Further concentration of the mother liquor yields a mixture of taurine and ammonium sulfate.

Example 2

Ethionic acid, 206 g, is diluted with 800 mL of deionized water and heated to reflux for three hours to complete the hydrolysis to an aqueous solution containing isethionic acid and sulfuric acid, to which 80 g of sodium sulfate is added. About 120 g of calcium hydroxide is added slowly to bring the pH to 8-9 and a white slurry of calcium sulfate is formed. After filtration and washing with deionized water, an aqueous solution of sodium isethionate is obtained.

Into a 2 L autoclave is added the solution of sodium isethionate, and 2 g of sodium hydroxide. The solution is then saturated with ammonia to about 25% of ammonia. Ammonolysis is carried out at 220° C. under the autogenous pressure of about 140 bar for 2 hrs. HPLC analysis indicates the formation of 110 g of taurine in the solution. After removal of the excess ammonia, sulfuric acid is used to liberate taurine to yield a mixture of taurine and sodium sulfate.

Example 3

Ethionic acid, 206 g, is diluted with 800 mL of deionized water containing 80 g of sodium sulfate. About 120 g of calcium hydroxide is added slowly to bring a pH to 7-8 while the temperature is controlled at 35-50° C., then to a pH of 10-11 while the temperature is raised to 70-80° C. from the heat of neutralization. The temperature of the slurry is maintained at 70-80° C. for about 1 hour and lowed to 50° C. Dilute sulfuric acid is used to adjust the pH of the slurry to 7-8. The formed sodium vinyl sulfonate is freed from the precipitated calcium sulfate by filtration and is obtained as a clear and virtually colorless solution.

To the aqueous solution of sodium vinyl sulfonate, placed in a 2 L autoclave, is saturated with ammonia to about 25%, and is added 2 g of sodium hydroxide. The ammonolysis reaction is carried out at 220° C. under the autogenous pressure of about 140 bar for 2 hours. HPLC analysis indicates the formation of 95 g of taurine in the solution. After removal of excess ammonia, sulfuric acid is used to neutralize the alkaline solution to a pH of 5-6 to yield a mixture of taurine and sodium sulfate.

It will be understood that the foregoing examples, explanation, drawings are for illustrative purposes only and that in view of the instant disclosure various modifications of the present invention will be self-evident to those skilled in the art and are to be included within the spirit and purview of this application and the scope of the appended claims.

What is claimed is:

1. A process for the production of taurine from ethanol, comprising:
   (a) reacting ethanol with sulfur trioxide to form ethionic acid;
   (b) converting ethionic acid to alkali isethionate, which comprises
      i. hydrolyzing ethionic acid to prepare a reaction mixture comprising isethionic acid and sulfuric acid;
      ii. adding alkali sulfate to said reaction mixture;
      iii. adding calcium oxide, calcium hydroxide, or calcium carbonate to said reaction mixture;
      iv. obtaining alkali isethionate from the reaction mixture;
   (c) reacting alkali isethionate with ammonia to form alkali taurinate at a temperature from 190 to 250° C., under the pressure from the autogenous to 250 bar in the presence of alkali metal salts as catalyst;
   (d) removing ammonia and neutralizing the reaction mixture to form taurine and alkali sulfate;
   (e) removing taurine and recycling alkali sulfate to step ii.

2. The process according to claim 1, wherein said alkali sulfate is selected from the group consisting of lithium sulfate, sodium sulfate, and potassium sulfate.

* * * * *